United States Patent [19]

Kroll

[11] Patent Number: 5,738,105
[45] Date of Patent: Apr. 14, 1998

[54] METHOD AND APPARATUS FOR SENSING R-WAVES USING BOTH NEAR FIELD AND FAR FIELD SENSING SIMULTANEOUSLY

[75] Inventor: Mark W. Kroll, Minnetonka, Minn.

[73] Assignee: Angeion Corporation, Plymouth, Minn.

[21] Appl. No.: 547,275

[22] Filed: Oct. 24, 1995

[51] Int. Cl.⁶ .................................................. A61B 5/0456
[52] U.S. Cl. .................................................. 128/708; 607/5
[58] Field of Search .................................. 607/4, 5, 6, 17; 128/696, 708

[56] References Cited

U.S. PATENT DOCUMENTS

| | | |
|---|---|---|
| 3,614,955 | 10/1971 | Mirowski et al. . |
| 4,202,340 | 5/1980 | Langer et al. . |
| 5,215,083 | 6/1993 | Drane et al. . |
| 5,265,602 | 11/1993 | Anderson et al. . |
| 5,269,300 | 12/1993 | Kelly et al. . |
| 5,275,621 | 1/1994 | Mehra . |
| 5,312,443 | 5/1994 | Adams et al. . |
| 5,330,512 | 7/1994 | Hauck et al. . |
| 5,331,966 | 7/1994 | Bennett et al. . |
| 5,366,487 | 11/1994 | Adams et al. . |

FOREIGN PATENT DOCUMENTS

93/20891  10/1993  WIPO .

*Primary Examiner*—George Manuel
*Assistant Examiner*—Scott M. Getzow
*Attorney, Agent, or Firm*—Patterson & Keough, P.A.

[57] ABSTRACT

The present invention is a R-wave sensing system for an implantable cardiac arrythmia therapy device. In particular the present invention is a system having local detection electrodes for sensing a local electrical signal representing cardiac activity in a local area of a patient's heart and having global detection electrodes for sensing a global electrical signal representing cardiac activity in a global area of the patient's heart. First and second amplifiers for amplifying the local and global electrical signals detected are provided as are first and second filters for filtering the detected signals. A converter is provided for converting the local electrical signal detected by the local detection electrodes into a digital signal so as to generate a masking pulse. Finally, a multiplier is provided for combining the masking pulse with the filtered global electrical signal to produce a correlation signal which represents a more accurate sensing of the R-waves based on a combination of the local and global electrical signals.

20 Claims, 4 Drawing Sheets

# METHOD AND APPARATUS FOR SENSING R-WAVES USING BOTH NEAR FIELD AND FAR FIELD SENSING SIMULTANEOUSLY

BACKGROUND

1. Field of the Invention

The present invention relates generally to a method for accurately sensing R-waves for cardioversion therapy for delivery by an implantable cardioverter defibrillator (ICD). More particularly, the present invention relates to a method for accurately sensing R-waves using both near field and far field sensing simultaneously for rate counting and determination of appropriate therapy by the ICD system.

2. Background of the Invention

The use of implantable cardioverter defibrillator (ICD) systems as a medical therapy for persons with abnormal heart conditions or arrhythmias is well known. Initially, ICD systems were used only to resuscitate or defibrillate a heart which had stopped pumping because there was no organized heart beat. This type of arrhythmia, referred to as ventricular fibrillation (VF), is relatively simple to detect and is fatal if not corrected in a few minutes. The general approach in using ICD systems to treat ventricular fibrillation is to deliver a relatively large electrical defibrillation countershock to electrodes implanted about the heart in an attempt to restart the electrical activity of the heart. In existing ICD systems, the defibrillation electrical countershocks are in the range of 25 to 40 joules, and are generated by high voltage capacitors within the ICD system that are charged to approximately 600 to 750 volts by one or more internal batteries.

ICD systems are now being used to treat other types of abnormal heart conditions, such as the main pumping chambers of the heart beating too fast. This type of arrhythmia, referred to as ventricular tachycardia (VT) can be clinically divided into two subclasses. The first VT subclass is a low rate ventricular tachycardia where the heart is beating in the range of approximately 120 to about 180 beats per minute. While a low rate VT is not normal, the patient is not in immediate danger of dying because there is still a perfusing pulse that can pump blood to the body. The second VT subclass is a high rate ventricular tachycardia where the heart is beating in the range of approximately 180 to about 250 beats per minute. In contrast to low rate VT, a patient with a high rate VT is in imminent danger of death within the next several minutes due to a significantly diminished or absent perfusing pulse.

High rate VT, despite its severity and grim prognosis, is treated differently from ventricular fibrillation. This is because, unlike a VF arrhythmia where there is no organized electrical activity of the heart, a high rate VT arrhythmia still exhibits a fairly organized and synchronous electrical activity of the heart and often can be treated by delivering a synchronized "cardioversion" countershock of lower energy that is in the range of 1 to 5 joules. If this cardioversion countershock is unsuccessful, existing ICD systems immediately resort to the use of a defibrillation countershock due to the serious nature of the high rate VT arrhythmia.

Low rate VT is also characterized by a synchronized electrical activity of the heart, but a low rate VT is usually able to generate a perfusing pulse. As a result, it is important in treating a low rate VT to avoid subjecting the patient to an electrical cardioversion therapy that could convert the patient from an abnormal, but life sustaining arrhythmia, to an abnormal and terminal arrhythmia. Because a low rate VT that is not inadvertently converted to a high rate VT is not an immediately life-threatening situation, avoidance of shock pain is a major goal for treating low rate VT. Thus, the usual approach for low rate VT is to deliver bursts of overdrive pacing pulses that will pace the heart at a rate greater than the low rate tachycardia. This technique utilizes pacemaker level energies of approximately 10 to 50 microjoules per pulse for a burst duration of approximately 10 pulses per burst. If the first burst is unsuccessful and the patient remains in a low rate VT, subsequent bursts are reattempted. Unfortunately, even this "Anti-tachycardia" pacing can cause acceleration of the rhythm into a high rate tachycardia or even fibrillation.

The ICD systems currently used have automatic triggering functions such that when a specified condition is detected, the ICD is automatically set into action. The automatic triggering of ICDs may be understood as divided into a two part detection mechanism which attempts first to sense each beat of the heart and second to analyze the pattern of the sensed beats over time by comparing the pattern to various diagnostic models with a goal of accurately assessing the patient's current heart condition. Many times the analytical second part uses logic to also consider the persistence of an undesirable beat rate pattern, the onset rapidity of the undesirable pattern, as well as physiological differences such as temperature changes, pH changes, etc., in the patient. Having classified or identified the undesirable condition, the ICD then provides treatment consistent with the condition identified.

The ability of ICDs to correctly and accurately detect and identify cardiac fibrillation and/or tachyrhythmia is quite important. False positive detection errors will apply an unrequited defibrillation or cardioversion countershock to a heart which in turn is both painful and potentially damaging. One possible cause of a false positive detection error is the naturally accelerated heart rate associated with vigorous exercise. False negative detection errors, on the other hand, will fail to timely apply a countershock to a fibrillating heart and may allow a patient to die for failure to trigger or allow more easily treatable conditions to persist or progress to more dangerous conditions. Alternatively, a temporary false negative may unduly delay application of a defibrillation or cardioversion shock treatment. Prompt detection and application of appropriate treatment, on the order of seconds or tens of seconds, is a key to successful treatment and any delays begin to reduce the likelihood of successful cardioversion and/or defibrillation.

No matter how sophisticated the analysis provided in the second part of the control mechanism, it is clear that sensing of the heart beats is critical. All the second part analytical models use the sensed heart rate as a major input to diagnosis.

Monitoring and detection of cardiac function typically involves electrical sensing of muscle and nerve cell depolarization which can be correlated with cardiac muscle contractions. Electrodes implanted in the heart at positions, such as those in which pacing electrodes might be placed, sense an electrical voltage which when considered over time are not unlike a typical surface electrocardiogram, yet are more defined and localized. Specifically, the electrocardiogram waveform under normal conditions includes a P wave, followed by a complex three part waveform called the QRS pattern, and then a T wave. Of these various components, the "R-wave" is the dominant amplitude feature and is therefore most typically used to sense a heart beat.

In very early defibrillator concepts, detection of the onset of a tachycardia or fibrillation was made by monitoring the loss of pressure. A system such as this is taught in U.S. Pat. No. 3,614,955. As it proved impractical to make a low power reliable implantable pressure sensor, the industry moved to detecting fibrillation by means of an electrocardiogram and its characteristics. An example of this detection is shown in U.S. Pat. No. 4,202,340.

Detection of ventricular tachycardia arrhythmias in currently available ICD's relies primarily on an evaluation of the sequence of ventricular event timing intervals obtained from a rate sense amplifier and comparator circuitry. The timing intervals are classified by comparing them to threshold conditions and depending upon the comparison, appropriate therapies may or may not be applied. Existing ICD's are typically equipped with sense amplifiers and provide a count of the rate of heart depolarizations. This is done in a similar fashion to the commonly used external heart monitoring systems using electrocardiogram wave forms. The source of the electrical signals for the implantable device also uses depolarization of the heart muscle, but the waveforms are slightly different due to the positioning of the sensing electrodes.

There are two general types of sensing electrodes. The first are global, or far field, electrodes which may be mounted on the surface of the heart, for example. These global electrodes see voltage wave forms which represent an averaging of the dynamic voltages from the heart muscle because they monitor a large area of the heart. The second general type of electrodes are local, or near field, electrodes. The local electrodes typically see a more precise wave form that represents the passage of a depolarization wave through a nearby section of the heart. The role of the sense amplifier is to detect the R-wave and mark each occurrence with a digital pulse suitable for accurate counting by other circuitry.

U.S. Pat. No. 5,257,621 to Bardy et al. discloses an apparatus for the detection of and discrimination between tachycardia and fibrillation and the treatment of both that uses both near field and far field sensing electrodes. The Bardy reference discloses sequentially measuring near field and far field signals and then using the time interval between the onset of the near field signal and the far field signal to detect fibrillation.

U.S. Pat. No. 5,366,487 to Adams et al., which is assigned to the assignee of the present application, the specification of which is herein incorporated by reference, discloses the detection of both near and far field signals. A delay is calculated between the near and far field signals and the delay is then manipulated to calculate the mean and standard deviation of the delays to determine ventricular fibrillation, ventricular tachycardia or normal sinus rhythm.

U.S. Pat. No. 5,331,966, issued to Bennett et al. discloses a method and apparatus of obtaining and detecting electrical cardiac signals via an array of closely spaced subcutaneous electrodes with suitable switching circuits. The electrodes are selectively or sequentially coupled in one or more pairs to process the signals across the pair. The signals are then stored and compared to one another to determine the sensing vector which provides the largest cardiac signal.

U.S. Pat. No. 5,330,512, issued to Hauck et al. describes a pacemaker for detecting ECG signals. A signal processing circuit is connected to a first and second reference electrode. Both the first and second reference electrodes are in a unipolar mode. The signal processing circuit has a means for adding the first and second signals from the electrodes to cancel out residual opposite polarized potentials.

U.S. Pat. No. 5,265,602, issued to Anderson et al. discloses a method and apparatus for measuring both electrocardiogram (ECG) and intracardiac electrogram (EGM) signals. A composite atrial and ventricular EGM signal is provided by a pacemaker for transmission via the pacemakers telemetry channel. Both leads used in the '602 patent are bipolar leads.

As stated above, accurate sensing of a patient's current heart condition is critical in applying an appropriate therapy. False positive detection errors may cause an unrequired defibrillation or cardioversion countershock to the heart which is both very painful and potentially damaging to the heart. False negative detection errors may cause the failure to timely apply a countershock to a fibrillating heart and thus may allow a patient to die. It would be desirable to provide an ICD capable of more accurate sensing of R-waves to provide for a more accurate diagnosis of arrhythmias.

SUMMARY OF THE INVENTION

The present invention is a R-wave sensing system for an implantable cardiac arrythmia therapy device. In particular the present invention is a system having local detection electrodes for sensing a local electrical signal representing cardiac activity in a local area of a patient's heart and having global detection electrodes for sensing a global electrical signal representing cardiac activity in a global area of the patient's heart. First and second amplifiers for amplifying the local and global electrical signals detected are provided as are first and second filters for filtering the detected signals. A converter is provided for converting the local electrical signal detected by the local detection electrodes into a digital signal so as to generate a masking pulse. Finally, a multiplier is provided for combining the masking pulse with the filtered global electrical signal to produce a correlation signal which represents a more accurate sensing of the R-waves based on a combination of the local and global electrical signals.

DETAILED DESCRIPTION

Figure 1:
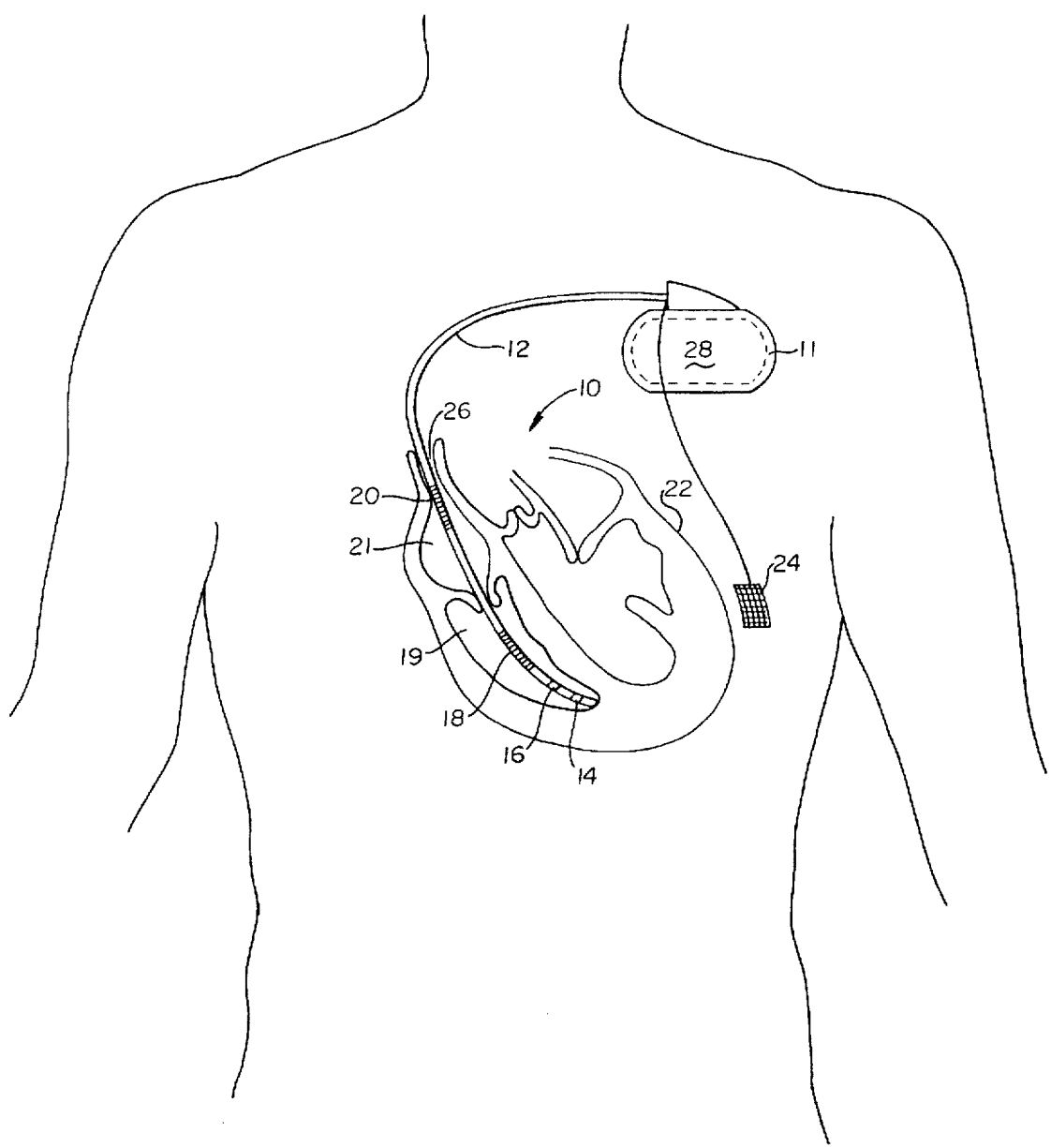
FIG. 1 is an implantable cardioverter defibrillator (ICD) system implanted in a human patient.
Figure 2:
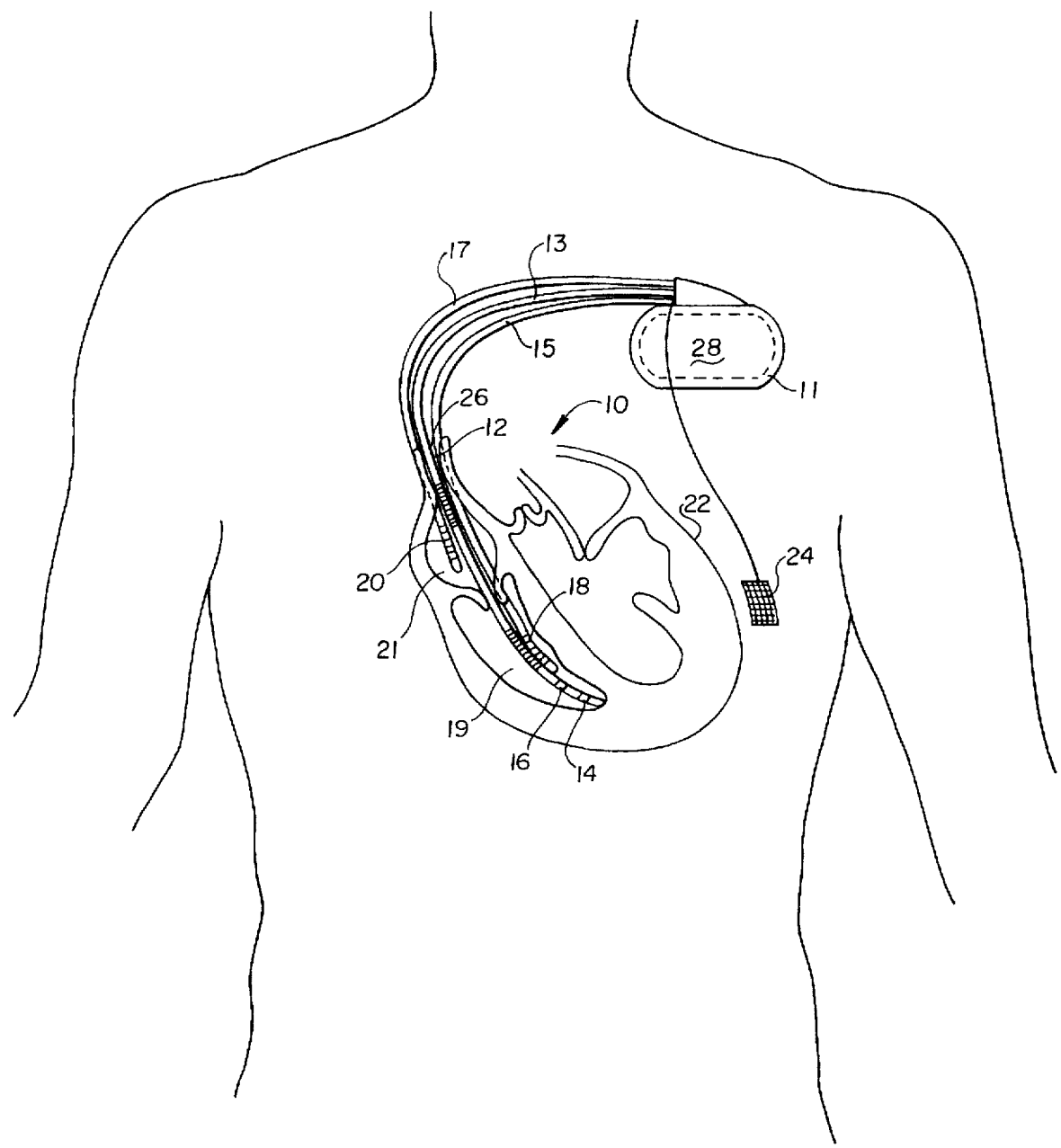
FIG. 2 is an implantable cardioverter defibrillator (ICD) system implanted in a human patient having multiple catheters.

The present invention is a R-wave sensing system and method for using the same, for an implantable cardioversion defibrillation (ICD) system. FIGS. 1 and 2 illustrate two known configurations for an ICD system 10. The ICD illustrated in FIG. 1 has a housing 11 and a conventional pacemaker-defibrillator catheter 12 connected to the housing. Catheter 12 carries bipolar pacing electrodes illustrated as tip electrode 14 and ring electrode 16, and two defibrillating electrodes 18, 20. Electrode 18 is positioned within the right ventricle 19 of the patient's heart 22 and electrode 20 is positioned within the right atrium 21 of the heart. Catheter 12 could also be positioned with at least one electrode in the supra vena cava 26. A subcutaneous patch 24 is illustrated for affixing to the external tissue of the heart 22. Alternatively, a catheter with at least one electrode could be positional in the coronary sinus artery 27. Housing 11 also forms an active housing electrode 28 which may be used for far field sensing as will be described below.

The ICD illustrated in FIG. 2 is very similar to that illustrated in FIG. 1 and like elements are correspondingly identified. ICD 10 has a housing 11 and attached to the housing are a plurality of commonly used catheters 13, 15, and 17. Catheter 13 carries bipolar pacing electrodes illustrated as tip electrode 14 and ring electrode 16. Catheter 15 carries defibrillating electrode 18 which is positioned within the right ventricle 19 of the patient's heart 22. Catheter 17 carries on it electrode 20 which is positioned within the right atrium 21 of the heart 22. Electrodes 18 or 20 could also be positioned in the supra vena cava 26 or coronary sinus artery 27 if desired. A subcutaneous patch 24 is illustrated for affixing to the external tissue of the heart 22. Housing 11 also forms an active housing electrode 28 which may be used for far field sensing as will be described below.

Figure 3:
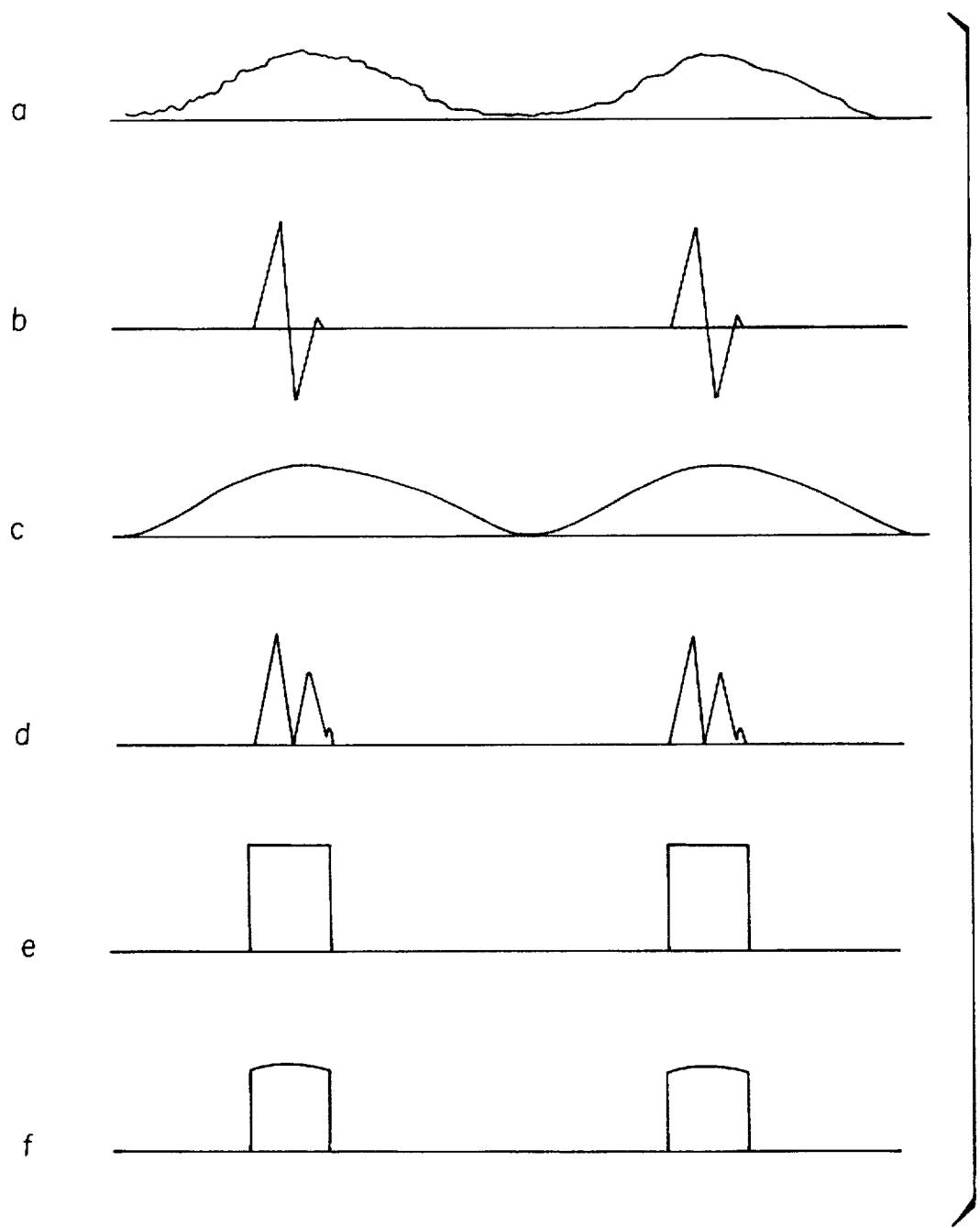
FIG. 3a is a trace of a far field signal.
FIG. 3b is a trace of a near field signal.
FIG. 3c is a trace of the signal from FIG. 3a filtered.
FIG. 3d is a trace of the signal from FIG. 3b filtered and rectified.
FIG. 3e is a trace of the near field signal from FIG. 3b filtered, rectified and digitized.
FIG. 3f is a correlation signal resulting from the combination of the signals in FIG. 3c and FIG. 3e.

FIG. 3a illustrates a trace of a far field signal taken by a far field (global) electrode pair. Far field electrodes are so classified because they have a relatively large surface area, having a total surface area of greater than 1 cm$^2$. The source of electrical signals sensed by the far field electrodes is an averaging of the dynamic voltages from heart 22 due to the depolarization of the heart. While the signals sensed by the far field electrodes is an averaging, the far field signals are also somewhat dependent upon the positioning of the electrodes. The far field electrode pair of the present invention could be formed from any of electrodes 18, 20, 24, or 28 with a sensing electrode such as tip electrode 14. It would also be possible to use other types of electrodes as far field electrodes, such as an external patch. As can be seen in FIG. 3a, the far field signal tends to be very noisy and has very shallow start and stop regions.

FIG. 3b is a trace of a near field (local) sensed signal. The near field signal sees a more precise wave form representing the passage of a depolarization wave through a nearby section of the heart. Near field electrodes are so classified because they have a relatively small surface area, having a total surface area of less than about 1 cm$^2$. An example of a near field sensing pair is the bipolar pair of electrodes 14, 16. As can be seen in FIG. 3b, the near field signal has very well defined start and stop regions and has a high amplitude. However, the location of the near field signal with respect to the overall QRS complex depends upon the location of the bipolar pair with respect to the main source of the ventricular tachycardia.

Figure 4:
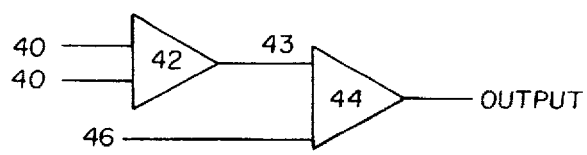
FIG. 4 is a general block diagram of a known detection amplifier and compare circuit.

FIG. 4 is a simplified block diagram of a known sensing system. A signal 40 is sensed by either a far field electrode pair or a near field electrode pair and the signal is then passed to an amplifier 42 which outputs an amplified signal 43. The output of amplifier 42 is passed to a comparator 44 for comparison to a threshold value 46. If amplified signal 43 is greater than threshold value 46, then the output of comparator 44 indicates that a R-wave has been detected by giving a pulse.

Amplifiers are necessary in ICD sensing systems because typically R-waves have a peak amplitude in the range of about 3-15 mV during normal sinus rhythm. Ideally, a threshold voltage would be set such that only R-waves would exceed it, which would put the threshold level somewhere about 3 mV. There are a couple of problems with having the threshold voltage at about 3 mV. The first problem is that it is difficult to make a 3 mV semiconductor reference. Typically in integrated circuits there are only a few readily available voltages to chose from, and none are near 3 mV. The second problem is that comparators have a random error associated with them that is greater than 3 mV, making reliable comparison an impossibility.

At this point reference may be made to a copending application entitled "IMPROVED R-WAVE DETECTION SYSTEM FOR IMPLANTABLE CARDIOVERTER DEFIBRILLATORS", Ser. No. 08/524,391, filed Sep. 6, 1995, which is assigned to the assignee of the present invention and which is hereby incorporated by reference. The '391 application discloses a method of determining a declining threshold of sensitivity used to recognize subsequent R-waves.

Figure 5:
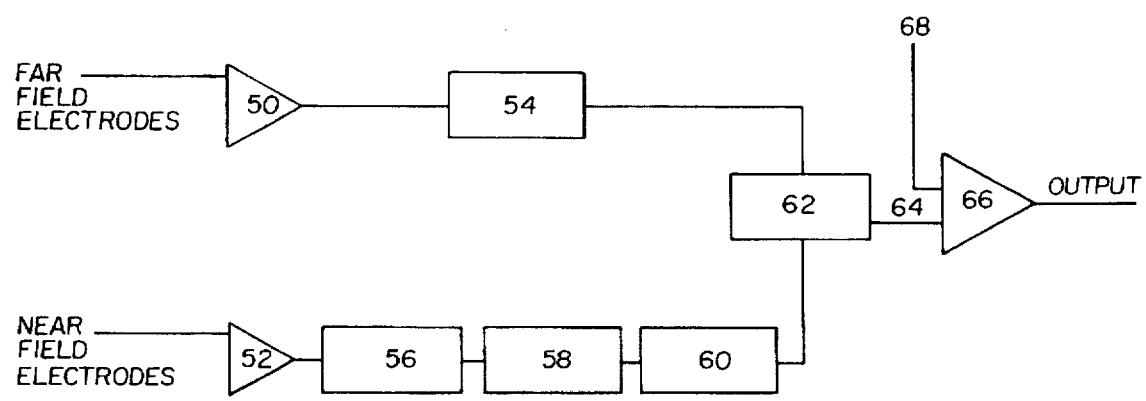
FIG. 5 is a general block diagram of the system of the present invention.

FIG. 5 is a general block diagram of the overall system of the present invention. As can be seen, the signals sensed by both the far field electrodes and the near field electrodes are passed through amplifiers 50, 52 respectively. Amplifiers 50, 52 have a gain of approximately 1000 in the preferred embodiment of the present invention. This allows the threshold voltage to be set at 3 V, which is a readily available voltage for comparison in typical integrated circuits.

The signals sensed by both the near field and far field electrodes are very noisy signals, and thus it is necessary to clean these signals up before interpreting them. The noise comes from many different sources, such as DC electrode offset voltages, baseline drift, electromyogram interference, and electromagnetic interference due to machinery and the like. The signals are cleaned up with filters 54, 56. Filters 54, 56 are a combination of both high pass and low pass filters. Typically bandwidths for sensing are from 10 Hz to 100 Hz. The high pass filter portion of filters 54, 56 of the present invention is designed to filter out all signals having a frequency greater than 100 Hz. It should be noted that greater or lesser frequency values may be chosen for the high pass filter portion without departing from the spirit or scope of the invention. The low pass filter portion of filters 54, 56 is designed to filter out all signals having a frequency less than 30 Hz. Once again it should be noted that greater or lesser frequency values may be chosen for the low pass filter portion without departing from the spirit or scope of the invention.

Once the near field signal has been amplified by amplifier 52 and filtered by filter 56, it is passed through a rectifier 58. Rectifier 58 is a full wave rectifier which is algebraically equivalent to an absolute value function. By rectifying the near field signal, both positive and negative going R-waves are accounted for. The rectified signal is illustrated in FIG. 3d.

After the near field signal has been rectified by rectifier 58, it is digitized by an analog to digital converter 60. The digitized near field signal is illustrated in FIG. 3e.

After the near field signal has been digitized by analog to digital converter 60, the amplified and filtered far field signal illustrated in FIG. 3c, and the amplified, filtered, rectified and digitized near field signal illustrated in FIG. 3e, are combined together in a multiplier 62. This function may be accomplished by utilizing a logical AND gate or any other commonly used circuitry for combining a masking signal with another signal. The resultant correlation signal 64 is illustrated in FIG. 3f.

Correlation signal 64 is then passed to a comparator 66 for comparison to a threshold value 68. As indicated above, threshold value 68 is initially set at 3 volts for the present invention. If correlation signal 66 is greater than 3 volts, then the output of comparator 64 indicates that a R-wave has been detected by giving a pulse. In a preferred embodiment, threshold value 68 is dynamically altered in the manner described in the copending application entitled "IMPROVED R WAVE DETECTION SYSTEM FOR IMPLANTABLE CARDIOVERTER DEFIBRILLATORS", Ser. No. 08/524,391, which was previously incorporated by reference.

The filtering, rectifying, digitizing and multiplying steps of the present invention may be accomplished utilizing discrete components. These steps may also be accomplished using a combination of discrete components and microprocessing. Additionally, the multiplication and comparison functions may be accomplished utilizing digital signal processing means without departing from the spirit or scope of the present invention.

By utilizing the teachings of the present invention, the benefits of both far field sensing and near field sensing are combined. The correlation signal has well defined start and stop regions as does the near field signal, it has a high amplitude, as does the near field signal, and it includes an averaging of electrical activity over a wide area as does the far field signal.

We claim:

1. An R-wave sensing system for an implantable cardiac arrythmia therapy device, the system comprising:
   local detection electrodes that sense a local electrical signal representing cardiac activity in a local area of a patient's heart;
   global detection electrodes that sense a global electrical signal representing cardiac activity in a global area of the patient's heart;
   a first filter that filters the local electrical signal so as to generate a masking pulse;
   a second filter that filters the global electrical signal; and
   means for combining the masking pulse with the filtered global electrical signal to produce a correlation signal representative of an R-wave sensed in the patient's heart.

2. The system of claim 1 further comprising a comparator electrically connected to the means for combining the masking pulse with the filtered global electrical signal that compares the correlation signal with a threshold signal for counting a rate at which R-waves are sensed.

3. The system of claim 1 further comprising first and second amplifiers electrically connected between the local detection electrodes and the first filter and between the global detection electrodes and the second filter to amplify the local and global signals, respectively.

4. The system of claim 1 further comprising a rectifier electrically connected to the first filter that rectifies the local electrical signal.

5. The system of claim 1 further comprising an analog to digital converter electrically connected to the first filter that converts the local electrical signal into a digital signal.

6. The system of claim 1 wherein the local detection electrodes have a surface area less than 1 cm$^2$.

7. The system of claim 1 wherein the global detection electrodes have a surface area greater than 1 cm$^2$.

8. An R-wave sensing system for an implantable cardiac arrythmia therapy device, the system comprising:
   local detection electrodes that sense a local electrical signal representing cardiac activity in a local area of a patient's heart;
   global detection electrodes that sense a global electrical signal representing cardiac activity in a global area of the patient's heart;
   a first amplifier that amplifies the local electrical signal;
   a second amplifier that amplifies the global electrical signal;
   a first filter that filters the local electrical signal;
   a second filter that filters the global electrical signal;
   a converter that converts the local electrical signal into a digital signal so as to generate a masking pulse; and
   a multiplier that multiplies the masking pulse with the filtered global electrical signal to produce a correlation signal representative of an R-wave sensed in the patient's heart.

9. The system of claim 8 further comprising a comparator electrically connected to the multiplier that compares the correlation signal with a threshold signal for rate counting of sensed R-waves.

10. The system of claim 8 further comprising a rectifier electrically connected to the first filter that rectifies the local electrical signal.

11. An R-wave sensing system for an implantable cardiac arrythmia therapy device, the system comprising:
    local detection means for sensing a local electrical signal representing cardiac activity in a local area of a patient's heart;
    global detection means for sensing a global electrical signal representing cardiac activity in a global area of the patient's heart;
    a first filtering means for filtering the local electrical signal so as to generate a masking pulse;
    a second filtering means for filtering the global electrical signal; and
    multiplication means for multiplying the masking pulse with the filtered global electrical signal to produce a correlation signal representative of an R-wave sensed in the patient's heart.

12. The system of claim 11 further comprising comparator means electrically connected to the multiplication means for comparing the correlation signal with a threshold signal for rate counting of sensed R-waves.

13. The system of claim 11 further comprising first and second amplifier means electrically connected to the local and global detection means, respectively for amplifying the local and global signals respectively.

14. The system of claim 11 further comprising rectification means electrically connected to the first filtering means for rectifying the local electrical signal.

15. The system of claim 11 further comprising conversion means electrically connected to the first filtering means for converting the local electrical signal into a digital signal.

16. A method of sensing R-waves in an implantable cardiac arrythmia therapy device, the method comprising the steps of:
    detecting local electrical signals of a patient's heart representing cardiac activity in a local area of the heart;
    detecting global electrical signals representing cardiac activity in a global area of the patient's heart;

filtering the local electrical signals so as to generate a masking signal;

filtering the global electrical signals; and combining the masking signal with the filtered global signals to produce a correlation signal representative of an R-wave sensed in the patient's heart.

17. The method of claim 16 further including the step of comparing the correlation signal with a threshold signal for rate counting of sensed R-wave.

18. The method of claim 16 further including the steps of amplifying the local and global signals.

19. The method of claim 16 further including the step of rectifying the local electrical signal.

20. The method of claim 16 further including the step of converting the local electrical signal into a digital signal.

* * * * *